US009285330B2

(12) United States Patent
Lee et al.

(10) Patent No.: US 9,285,330 B2
(45) Date of Patent: Mar. 15, 2016

(54) CALORIMETRIC MICROFLUIDIC SENSOR (71) Applicant: Marquette University, Milwaukee, WI (US)

(72) Inventors: Chung Hoon Lee, Brookfield, WI (US); Benyamin Davaji, Milwaukee, WI (US)

(73) Assignee: Marquette University, Milwaukee, WI (US)

( * ) Notice: Subject to any disclaimer, the term of this patent is extended or adjusted under 35 U.S.C. 154(b) by 199 days.

(21) Appl. No.: 14/230,876

(22) Filed: Mar. 31, 2014

(65) Prior Publication Data

US 2014/0303019 A1 Oct. 9, 2014

Related U.S. Application Data (60) Provisional application No. 61/808,420, filed on Apr. 4, 2013.

(51) Int. Cl.
| | |
|---|---|
| *G01N 25/48* | (2006.01) |
| *G01N 33/543* | (2006.01) |
| *C12Q 1/54* | (2006.01) |
| *C12Q 1/25* | (2006.01) |
| *G01K 17/00* | (2006.01) |
| *G01K 17/08* | (2006.01) |
| *B01L 3/00* | (2006.01) |

(52) U.S. Cl.
CPC .......... *G01N 25/4886* (2013.01); *B01L 3/5023* (2013.01); *C12Q 1/25* (2013.01); *C12Q 1/54* (2013.01); *G01K 17/006* (2013.01); *G01K 17/08* (2013.01); *G01N 33/54373* (2013.01); *B01L 2200/147* (2013.01); *B01L 2300/0627* (2013.01); *B01L 2300/0825* (2013.01); *B01L 2300/126* (2013.01); *B01L 2400/0406* (2013.01); *Y10T 436/143333* (2015.01)

(58) Field of Classification Search
None
See application file for complete search history.

(56) References Cited

U.S. PATENT DOCUMENTS

| | | | | |
|---|---|---|---|---|
| 4,589,072 | A | * | 5/1986 | Arimatsu ............... B01J 19/004 264/40.1 |
| 5,967,659 | A | | 10/1999 | Plotnikov et al. |
| 6,193,413 | B1 | | 2/2001 | Lieberman |
| 6,764,215 | B2 | | 7/2004 | Meyler et al. |
| 7,473,031 | B2 | | 1/2009 | Wolkin et al. |
| 8,201,992 | B2 | | 6/2012 | Horovitz et al. |
| 2003/0008286 | A1 | | 1/2003 | Zou et al. |

(Continued)

OTHER PUBLICATIONS

Ellerbee, et al. "Quantifying Colorimetric Assays in Paper-Based Microfluidic Devices by Measuging the Tranmission of Light through Paper", 2009 pp. 8447-8452, Analytical Chemistry, vol. 81, No. 20.

*Primary Examiner* — Jill Warden
*Assistant Examiner* — Timothy G Kingan
(74) *Attorney, Agent, or Firm* — Andrus Intellectual Property Law, LLP (57) ABSTRACT

A microfluidic sensor includes a microchannel that includes a reaction site with a reagent and a sample inlet. A liquid substance is received at the sample inlet and travels by capillary action to the reaction site. A temperature sensor measures a temperature as a result of a reaction between the reagent and a chemical in the liquid substance. A controller is communicatively connected to the temperature sensor, receives the temperature measured by the temperature sensor, and derives a concentration of the chemical in the liquid substance from the temperature.

20 Claims, 5 Drawing Sheets

(56) References Cited

U.S. PATENT DOCUMENTS

| | | | |
|---|---|---|---|
| 2003/0014193 A1* | 1/2003 | Ramsden | G01N 25/4846 702/136 |
| 2003/0016725 A1 | 1/2003 | Whateley et al. | |
| 2003/0059807 A1* | 3/2003 | Roach | C12Q 1/6825 435/6.11 |
| 2004/0038228 A1 | 2/2004 | Verhaegen | |
| 2004/0039298 A1* | 2/2004 | Abreu | A61B 3/1241 600/558 |
| 2005/0076943 A1* | 4/2005 | Cooper | G01N 25/482 136/224 |
| 2007/0207450 A1* | 9/2007 | Rodgers | B01J 19/0046 435/3 |
| 2011/0111517 A1* | 5/2011 | Siegel | B01L 3/502707 436/164 |
| 2013/0029851 A1 | 1/2013 | Esfandyarpour et al. | |
| 2014/0092935 A1* | 4/2014 | Lin | G01N 25/48 374/10 |

* cited by examiner

CALORIMETRIC MICROFLUIDIC SENSOR

CROSS-REFERENCE TO RELATED APPLICATION

The present application claims priority of U.S. Provisional Patent Application No. 61/808,420, filed on Apr. 4, 2013, the content of which is hereby incorporated herein by reference in its entirety.

BACKGROUND

The present disclosure is related to the field of chemical sensing. More specifically, the present disclosure is related to a paper-based microfluidic calorimetric chemical sensor.

Common paper-based chemical sensors use a paper strip to absorb a fluid that is to be tested for the presence of a substance. Paper strip chemical sensors often use colormetric detection, wherein some or all of the paper strip changes color when exposed to liquid having the chemical to be tested for. One such accommodating sample is a pregnancy test wherein at least a portion of the testing strip changes color in the presence of the hormone HCG. Colormetric sensors are generally limited to qualitative detections of the presence of a chemical substance. Colormetric sensors have limited, if any, ability to convey quantitative measures. Such quantitative results are reported by various color changes that are associated with bands or bins of concentration values.

Another form of paper-based chemical sensor is an electrochemical sensor whereby a chemical reaction/interaction with the substance to be measured yields a conductive byproduct resulting in a variable electrical response when energization is applied to the by-product. One example of these such systems is a blood glucose meter. While the electrochemical detection enables a quantitative measurement of the concentration or amount of the substance to be measured, recent studies have shown that these quantitative determinations can have a large error. Furthermore, electrochemical detection requires a chemical reaction that yields conductive by-products. This specialized reaction by-product limits the substances that may be sensed with these types of paper-based chemical sensors.

Thermal detection methods have been previously used to explore chemical interactions. However, currently available macro-scale calorimeter solutions are impractical for use in disposable and inexpensive sensing applications.

BRIEF DISCLOSURE

An exemplary embodiment of microfluidic sensor includes a microchannel. The microchannel includes a reaction site with a reagent. The microchannel further includes a sample inlet. The microchannel is configured to receive a liquid substance comprising a chemical at the sample inlet that travels by capillary action to the reaction site. A temperature sensor is located proximate the reaction site of the microchannel. The temperature sensor is configured to measure a temperature as a result of a reaction between the reagent and the chemical in the liquid substance. A controller is communicatively connected to the temperature sensor. The controller receives the temperature measured by the temperature sensor and derives a concentration of the chemical in the liquid substance from the temperature.

An exemplary embodiment of a microfluidic sensor system includes at least one microfluidic sensor. The microfluidic sensor includes a microchannel that includes a reaction site with a reagent. The microchannel further includes a sample inlet. The microchannel is configured to receive a liquid substance that includes a chemical at the sample inlet. The liquid substance travels by capillary reaction to the reaction site. The microfluidic sensor includes a temperature sensor located proximate the reaction site of the microchannel. The temperature sensor is configured to measure a temperature as a result of a reaction between the reagent and the chemical in the liquid substance. A controller is communicatively connected to the at least one microfluidic sensor. The controller receives the temperature measured by the temperature sensor of the at least one microfluidic sensor. The controller derives a concentration of the chemical in the liquid substance from the temperature. A graphical display is operated by the controller to present the derived concentration of the chemical and the liquid substance.

An exemplary embodiment of a method of chemical sensing includes selecting a reagent specific to a chemical to be sensed. A microfluidic sensor is provided. The microfluidic sensor includes a microchannel that includes a sample inlet and a reaction site that includes the selected reagent. The microfluidic sensor further includes is temperature sensor located proximate the reaction site. A liquid sample is received at the sample inlet. The liquid sample travels to the reaction site by capillary action. A temperature at the reaction site is measured. The temperature at the reaction site changes due to a reaction between the reagent and the chemical to be sensed. A change in the detected temperature is calculated. A determination is made from the change in temperature if the chemical to be sensed is present in the liquid sample. The determination is visually presented.

DETAILED DISCLOSURE

In the present disclosure, the temperature changes resulting from endothermic or exothermic reactions are used to detect and/or quantify the concentrations of targeted chemical substances. As used herein, chemical and/or chemical reaction is to be interpreted in an inclusive sense to include, but is not be limited to physical, organic, or bio-chemicals and associated reactions and also include, but not be limited to, proteins and enzymatic reactions. Paper-based microcalorimetric devices, as disclosed herein, offer a number of advantages: small volume of required sample, ease of sample handling, increased sensitivity at micro-scale, and low-cost manufacturing. In a microscale calorimeter, the heat generated or absorbed from a chemical reaction causes a temperature change, which depends on the concentration of the sample and reagents and the change in enthalpy of the reaction. The sensitivity of the temperature detection of a calorimeter is inversely proportional to the heat capacity of the calorimeter. A temperature change due to heat generated in a reaction can be expressed by:

$$\Delta T = (1/C_p)\Delta Q \tag{1}$$

where T is the temperature, Q is the heat, and Cp is the heat capacity.

Figure 1:
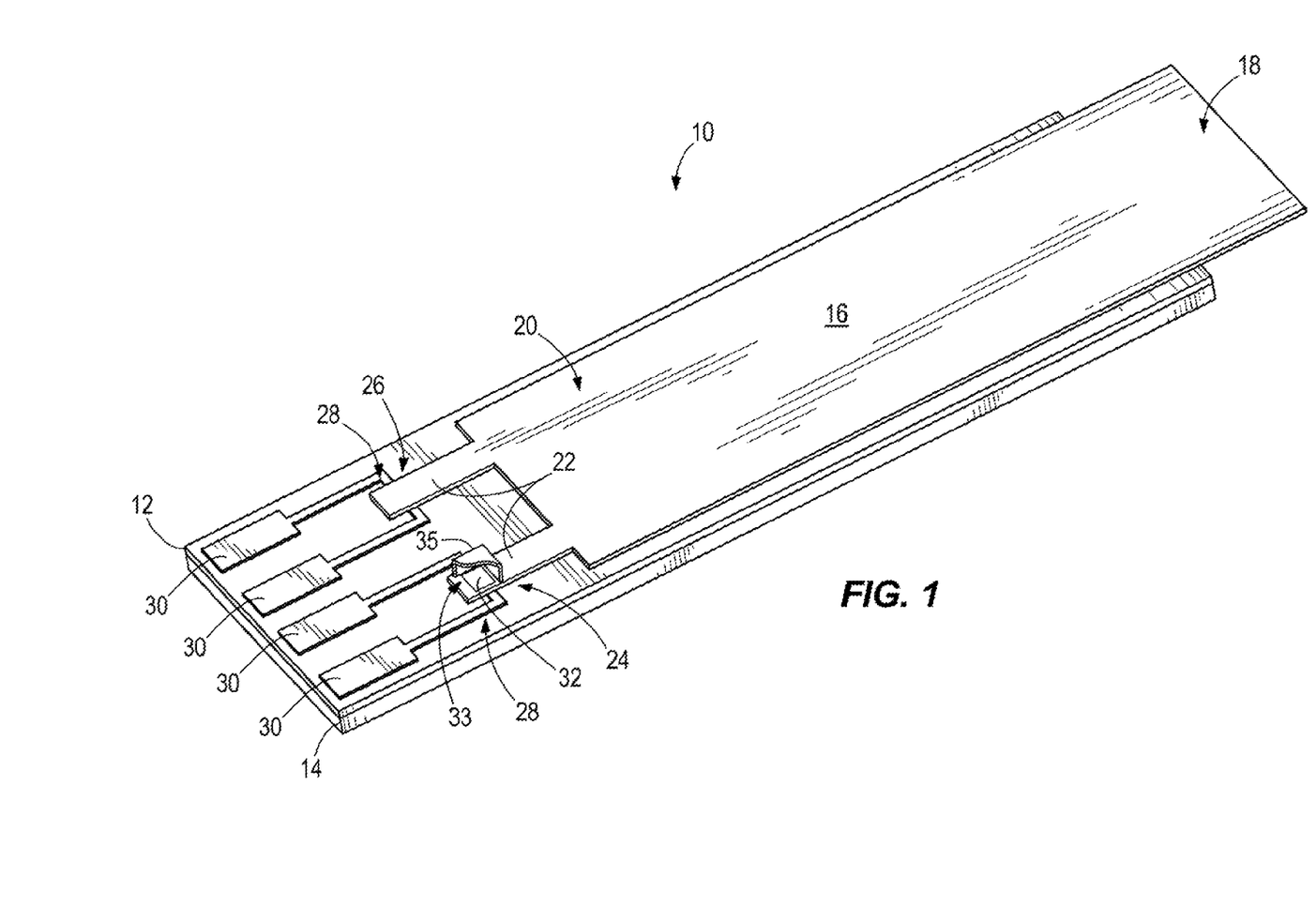
FIG. 1 depicts an exemplary embodiment of a calorimetric microfluidic sensor as disclosed herein.

FIG. 1 depicts a microfluidic sensor 10. The microfluidic sensor 10 is exemplarily constructed of an adhesive layer 12, exemplarily constructed a silicon or acrylic, secured to a support layer 14. In one embodiment, the support layer 14 is a polyamide support layer and in another embodiment, is a glass substrate support layer. A microfluidic channel 16, which may, in an embodiment, be a microchannel constructed of a paper sheet which extends past the support layer 14 and the adhesive layer 12. It is to be recognized that in alternative embodiments the microfluidic channel 16 may be any absorptive or porous material such that when a liquid that includes a substance to be tested is applied to the first end 18 of the microfluidic channel 16, the liquid (and the substances to be measured) is drawn to the second end 20 of the microfluidic channel 16. The liquid (and the substance to be measured) is drawn into the fingers 22 of the microfluidic channel 16. In an embodiment of a microfluidic sensor 10, the use of a microfluidic channel 16 to transfer the sample to be tested to the sensors helps to reduce any risk of microbubbles in the liquid/sample. In microfluidic applications, such microbubbles can create error in sensing applications and are therefore desired to be avoided.

The fingers 22 respectively terminate at a first sensor assembly 24 and a second sensor assembly 26. As will be explained in further detail herein, the exemplary embodiment of the microfluidic sensor 10 is exemplarily arranged as a differential sensor to compare a temperature change between the first sensor assembly 24 and the second sensor assembly 26. Both of the first sensor assembly 24 and the second sensor assembly 26 include temperature sensors 28 which are exemplarily resistive temperature detectors (RTD) 28. The RTDs are resistive elements that change in resistance relative to the temperature. By applying a constant voltage or current through the RTD, changes in the resistance of the RTD can be measured and, when calibrated, these resistance changes are correlated to a resulting temperature of the RTD. The first sensor assembly 24 and the second sensor assembly 26 include electrical contact pads 30 connected to either end of the RTD 28 through which the electrical excitation current can be applied.

The first sensor assembly 24 further includes a reagent 32 positioned at a reaction site relative to the RTD 28 and the finger 22 of the microfluidic channel 16. The reagent is selected such that the reagent chemically reacts with the chemical substance to be measured by the microfluidic sensor 10. In chemical applications, such reagent may be another reactive chemical while in biological applications, the reagent 32 may exemplarily be a protein or enzyme that reacts with the chemical substance to be sensed.

In operation, a liquid sample to be tested is applied to the first end 18 of the microfluidic channel 16. In exemplary embodiments, the microfluidic sensor 10 may be used to determine the presence of a substance, or in other embodiments, the concentration of the substance in the liquid sample. The liquid sample travels along the microfluidic channel 16, exemplarily through capillary action into the finger 22 of the first sensor assembly 24. When the substance to be measured comes in contact with the reagent 32, the chemical reaction occurs. All chemical reactions/interactions result in a change in entropy. Exothermic reactions release energy and increase the surrounding temperature. Endothermic reactions absorb energy twin the surrounding area, thereby reducing the temperature. Thus, every chemical reaction results in a change in enthalpy in the system that if the pressure and volume of the system remain constant, will result in a temperature change, that if directed to the RTD, can be sensed and quantified.

An exemplary embodiment seeks to achieve an adiabatic condition in which all of the heat exchange from the reaction is directed to temperature change of the RTD 28. In implementation, therefore it is desirable to direct as much of the entropy change to the RTD 28 of the first sensor assembly 24. Therefore, in embodiments, various features function to minimize heat loss, and other features are implemented to quantify the heat loss for calibration of the system. In an exemplary embodiment, the RTD 28, finger 22, and reagent 32 are surrounded by an insulative layer 33 to prevent or eliminate the release of energy into the area surrounding the first sensor assembly 24, and direct the entropy change to the RTD. In a non-limiting embodiment, this is achieved by encapsulating the RTD 28, reagent 32, and finger 22 with an insulative material. In one such embodiment, the insulative layer 33 may be a layer of air about these components. Air may be used in embodiments as air has a high thermal resistivity. In an embodiment, such insulative layer 33 of air is established by an enclosure 35 constructed of a further insulative material. The enclosure 35 can further function to suppress the convection of the layer of air, as convection of air can be a path of thermal loss. Radiation is also a thermal loss pathway; however, in embodiments, radiation is only a significant source of heat loss at high differentials between a reaction and the surroundings. In exemplary embodiments, the radiation losses are negligible as most chemical reactions result in lower temperature ranges than those required for radiation loss to be significant.

In an embodiment that uses a layer of air to achieve some of the thermal isolation for the sensor, the insulative layer 33 of air is contained within a small enclosure 35 of insulative material that helps to prevent heat loss or transfer due to convection. Furthermore, embodiments of the sensor include structures around the sensor that have a small thermal mass such that the heat energy given off by the chemical reaction/interaction is directed into the RTD sensor. The thermal mass is kept at a minimum, for example, in embodiments, since the paper layer 16 is very thin and the sensor uses a small volume of sample liquid and substance to be measured that reacts with the reagent. Therefore, with a minimized thermal mass and thermal isolation around the RTD, the energy change due to the chemical reaction/interaction can be accurately measured with the RTD.

The amount of heat lost to the surroundings can be characterized by a thermal time constant, which is a function of a heat capacity of the system and a thermal resistance between the calorimeter and the rest of the system. Using a first order approximation, the thermal time constant of the system can be expressed as, $$\tau = R_{th} C_p \quad (2)$$

where $R_{th}$ is the thermal resistance, and $C_p$ is the thermal capacity of the system, respectively.

The $R_{th}$ can be calculated as, $$R_{th} = L/(kA) \quad (3)$$

for material bounded surface, and $$R_{th} = 1/(4kr) \quad (4)$$

for air bounded surface, where L is the length along the heat flow direction, k is the thermal conductivity of material, A is the area perpendicular to the heat flow, and r is the radius of area:

The total heat capacity can be expressed as, $$C_p = C_{pg} + C_{ppl} \quad (5)$$

where $C_{pg}$ is the heat capacity of the substrate and Cppl is the heat capacity of the paper microfluidic channel and liquid. The heat capacity can be expressed as, $$C_p = \rho V_{cp} \qquad (6)$$

Where ρ is the mass density of the material, V is the volume and $c_p$ is the constant volume specific heat of the material.

Figure 2:
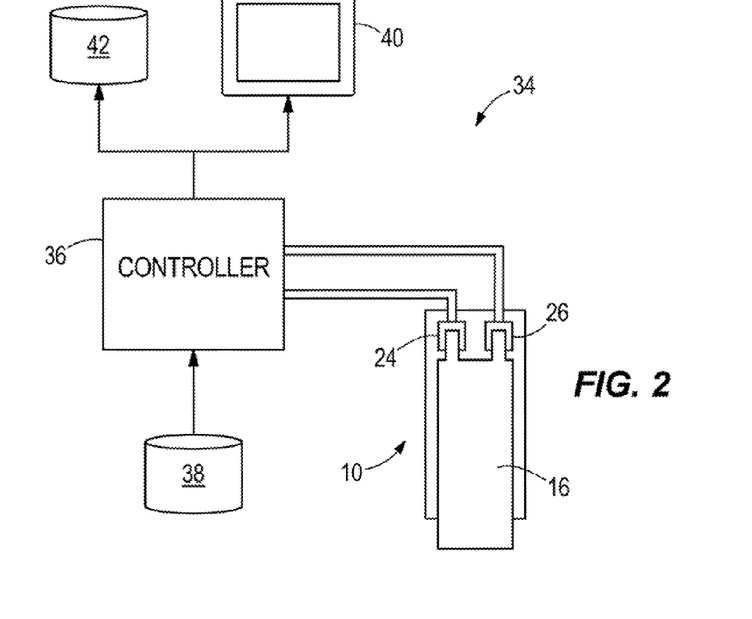
FIG. 2 is a schematic diagram of a system for sensing a chemical.

FIG. 2 depicts an embodiment of a chemical sensing system 34. The system 34 includes a controller 36, which may be any of a variety of digital processor, CPU's, controllers, or circuits, and may include, but not be limited to, lab-on-a-chip devices, such as to be used with microfluidic embodiments as disclosed herein. A microfluidic chemical sensor 10, an embodiment of which is described above in greater detail with respect to FIG. 1, is electrically connected to the controller 36. The controller 36 is communicatively connected to a computer readable medium 38 upon which computer readable code is stored. Upon execution of the computer readable code stored on the computer readable medium 38, the controller 36 performs the functions as described herein to measure the change in thermal energy in the sensor 10 and provide an indication of such results. In embodiments, the computer readable medium 38 may be an integral part of the controller 36, or may be a separate component that is operably and communicatively connected to the controller 36.

With respect to FIGS. 1 and 2, in operation, the chemical sensor 10 is configured to sense a particular substance by the inclusion of a reagent 32 in the first sensor assembly 24 that chemically reacts with the substance to be sensed. The computer readable medium 38 includes computer readable code, such that the controller 36, upon execution of the computer readable code, can measure a change in temperature due to the chemical reaction and translate this measured change in temperature into a concentration of the substance to be sensed. The substance is present in a liquid, such as water, which is exposed to the paper sheet 16 and through capillary action is drawn through the paper sheet 16 into the first sensor assembly 24 and the second sensor assembly 26. As previously noted, a reagent is located in the first sensor assembly 24 that chemically reacts with the substance to be measured. This chemical reaction produces a change in thermal energy due to the chemical reaction either being exothermic or endothermic in nature. The controller 36 is electrically connected to the RTD 28 of the first sensor assembly and measures the change in resistance of the RTD which translates into a measured temperature change.

The second sensor assembly 26 does not include a reagent and is used as a reference sensor, such as to account for changes in the operation of the sensor due to either temperature of the substance to the sensed, conductivity of the substance to be sensed, or other such properties independent of the chemical reaction/interaction that takes place in the first sensor assembly 24. The processor uses the resistance of the RTD 28 in the second sensor assembly 26 as a control for noise reduction in the resulting temperature measurement.

As previously stated, the controller 36 operates to measure the change in temperature due to the chemical reaction in the first sensor assembly 24. The controller 36 also operates to measure the temperature of the second sensor assembly 26. The controller 36 calculates a differential temperature, exemplarily by subtracting the temperature from the second sensor assembly 26 from the temperature from the first sensor assembly 24 to remove environmental effects on the temperature measurement. The controller then translates the measured changes in differential temperature to a concentration of the substance to be measured. As an output, the controller 36 can exemplarily present the change in temperature, sensed concentration of the substance to be sensed, or presence of the substance to be sensed on a graphical display 40. In an alternative embodiment, controller 36 may be connected to a computer readable medium 42 upon which the controller 36 causes the measured temperature change and/or the calculated substance concentration or presence to be stored for later access and retrieval.

Figure 3:
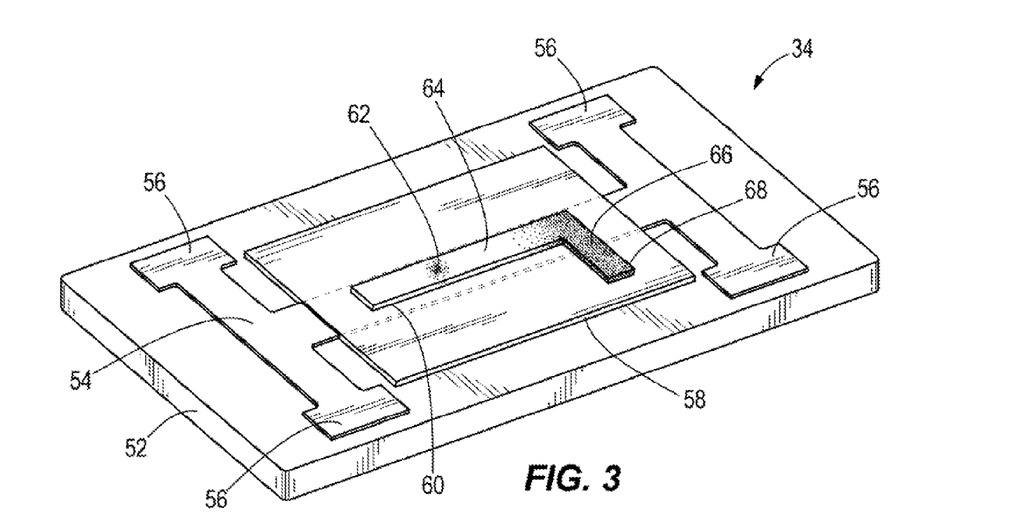
FIG. 3 depicts an additional exemplary embodiment of a calorimetric microfluidic sensor.

FIG. 3 depicts an additional exemplary embodiment of a microfluidic chemical sensor 50. It will be recognized that the additional embodiment presented herein is merely exemplary and that alternatives, including combinations of features disclosed in different embodiments presented herein are within the scope of the disclosure. The microfluidic chemical sensor 50 is exemplarily constructed on a support layer 52 which is exemplarily a glass substrate. In a non-limiting example, the glass may be 100 μm thick.

A resistive temperature detector (RTD) 54 is secured to the support layer 52. In embodiments, the RTD may be constructed of platinum, but in another exemplary embodiment, the RTD is constructed of an evaporated thin nickel film. In the exemplary embodiment of the microfluidic chemical sensor 50 depicted in FIG. 3, the RTD is arranged in a four-point configuration with four electrical contact pads 56. In an embodiment, the four-point configuration can eliminate the effects of junction resistance and thermal fluctuation of electrical leads on the resistance measurement of the RTD 54. As will be disclosed in further detail herein, the RTD 54 is dimensioned to be wider than the microfluidic channel 60 and more specifically, a reaction arm 64 of the microfluidic channel 60, in order to maximize the empathy change from the chemical reaction/interaction occurring at the reaction site 62 of the microfluidic channel directed into the RTD 54 in order to change the resistance of the RTD 54.

An adhesive layer 58, which may exemplarily be an acrylic film, and which may further be an acrylic film 5 mm thick is disposed over the RTD 54 and the support layer 52 and below the microfluidic channel 60. The adhesive layer 58 provides electrical isolation between the microfluidic channel 60 and the RTD 54 as well as helps to secure the microfluidic channel 60 to the support layer 52.

The microfluidic channel 60 provides transport of a liquid sample by capillary action to the reaction site 62. This eliminates the need for actuation or pumping and any associated valves required to control sample flow as are required in many microfluidic devices. A further advantage of the microfluidic channel 60 is that the capillary action provides bubble-free operation. The microfluidic channel 60 is exemplarily constructed of a paper (e.g. cellulose fibrous network) while in other embodiments porous glass or other materials may be used.

The microfluidic channel 60 may exemplarily be cut from paper using a CNC, knife plotter, or similar machine. The precision achieved of the CNC or knife plotter cut microfluidic channel 60 further enables shapes or constructions of the microfluidic channel 60 designed to control the test sample and reagent flow in the microfluidic channel 60. This method of manufacture also results in a minimal chemical contamination of the exemplary cellulose fibers of the microfluidic channel and may be heat treatment free which further eliminates a source of defect or chemical diffusion in the cellulose fiber. This helps to ensure that the liquid sample reaches the reaction site without contamination.

In the exemplary embodiment of the paper-based microfluidic chemical sensor 50 depicted in FIG. 3, the microfluidic channel is in a "L" shape with a reaction arm 64 and a sample arm 66. The perpendicular arrangement between the reaction arm 64 and the sample arm 66 minimizes mechanical stress caused from the introduction of the sample liquid to the chemical sensor. While the exemplary embodiment depicted in FIG. 3 is of an "L" shape it will be recognized that alternative shapes for constructions of the microfluidic channel 60 may be used in alternative embodiments, including "F" or "T" shaped in which multiple sample arms are available for the introduction of the sample liquid. In embodiments, the sample arm 66 extends outside of the RTD 54 and terminates in a sample inlet 68. In use, as will be described in further detail herein, the sample liquid is introduced in the sample inlet and is transported by capillary action towards the reagent located at the reaction site 62. Once the reagent comes in contact with the sample liquid, the reaction starts occurring.

As recognized above, embodiments of the microfluidic chemical sensor as disclosed herein may be used in a variety of settings and/or applications. These include, but are not limited to the analysis of chemical reactions to determine glucose concentration, determine concentration or presence of DNA, or to detect an onset of protein binding. While it is recognized that other embodiments or applications may be used, a further discussion of these exemplary applications is provided herein in order to provide additional details of embodiments of the microfluidic chemical sensor and use thereof.

Figure 5:
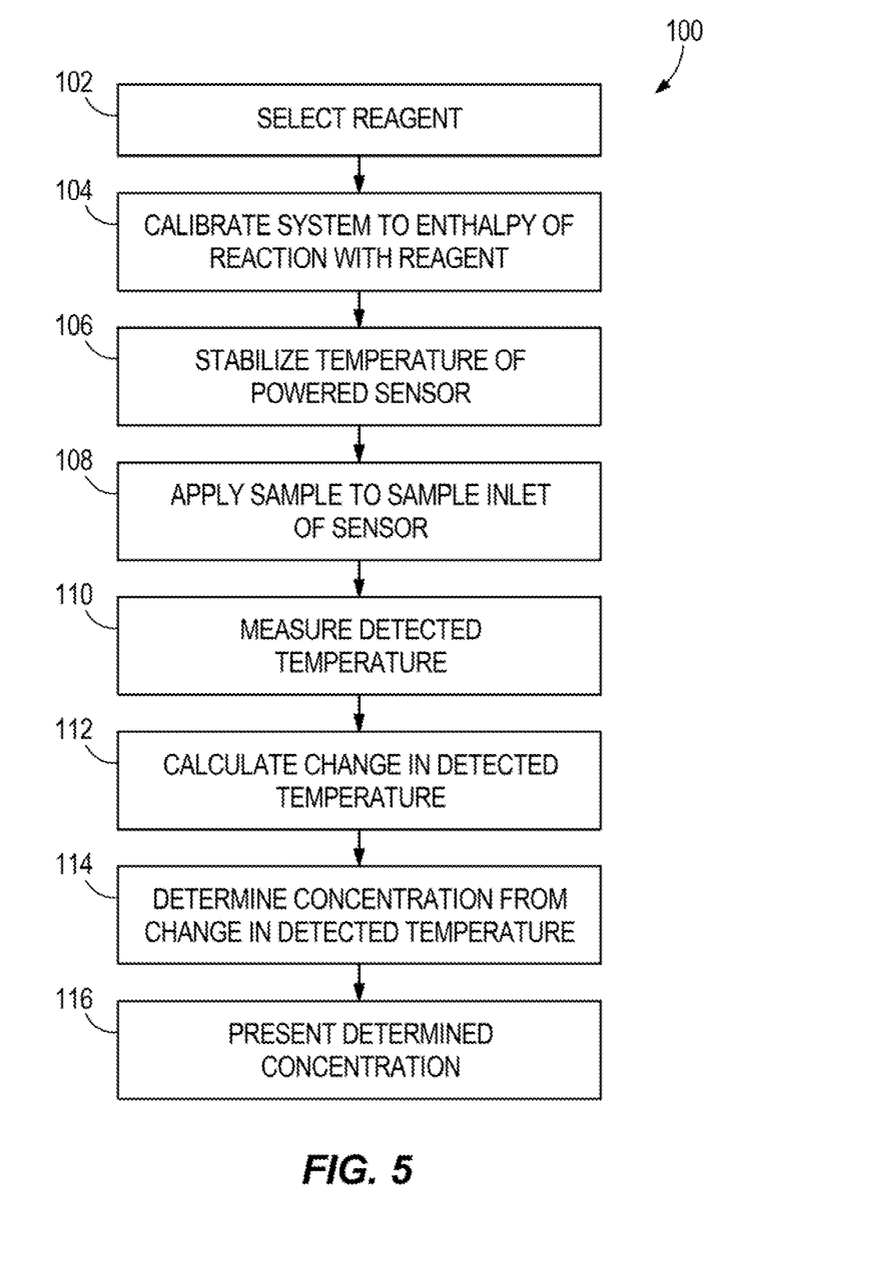
FIG. 5 is a flow chart of an exemplary embodiment of a method of sensing a chemical.

FIG. 5 is a flow chart that depicts an exemplary embodiment of a method 100 of sensing chemical concentration which will be described in further detail herein with respect to the example of a glucose level detection. In an exemplary embodiment, of the method, a reagent is selected at 102. In an embodiment, the glucose oxidase (GOD) enzyme is selected as the reagent to detect the glucose level by oxidation of glucose. In an embodiment, election of the reagent is specifically done to achieve a chemical reaction/interaction with the substance to the detector or measured with further consideration toward the enthalpy of such reaction in order to maximize the enthalpy change cause by the reaction. Therefore in an embodiment, the selection of the reagent may either be the selection of a reagent to place in a microfluidic chemical sensor or the selection of a microfluidic chemical sensor that incorporates the specific reagent for detection or measurement of the sample chemical.

At 104 the system is calibrated to the enthalpy of the expected reaction between the target chemical and the selected reagent. In the exemplary embodiment of glucose level detection, the reaction of glucose with the GOD enzyme causes an enthalpy change of $\Delta H = -80$ kJ/mol. The GOD enzyme reagent is located at the reaction site 62 of the reaction arm 64. In an exemplary embodiment, the area of the reagent was approximately ⅓ of the area of the microfluidic channel or reaction site, while in another embodiment is 45%, of the area of the microfluidic channel or reaction site, although these are merely exemplary. In operation, a bias current is applied across the RTD and a voltage drop across the RTD is measured. It has been recognized by the inventors that the RTD heats during operation due to resistive heating. In an exemplary embodiment, a 1 mA current through the RTD resulted in 0.11 mW of Joule heating, which elevated the RTD temperature by approximately 1-2° C. above the room temperature. At 106, the microfluidic chemical sensor is held with the RTD in a powered condition until the temperature of the RTD sensor stabilizes. Once the RTD sensor temperature stabilizes at 106, the sample (at room temperature) is applied to the sample arm of the sensor at 108. In an embodiment, the sample inlet and/or the microchannel of the sensor is constructed of paper (e.g. a cellulose fiber network). The liquid sample travels by capillary action up the sample inlet to the reaction arm. The temperature differential between the powered RTD and the liquid sample causes a cooling effect on the RTD. This is exemplarily due to both the relative cooler temperature of the liquid sample as well as evaporation from the liquid sample to the surroundings.

Figure 6:
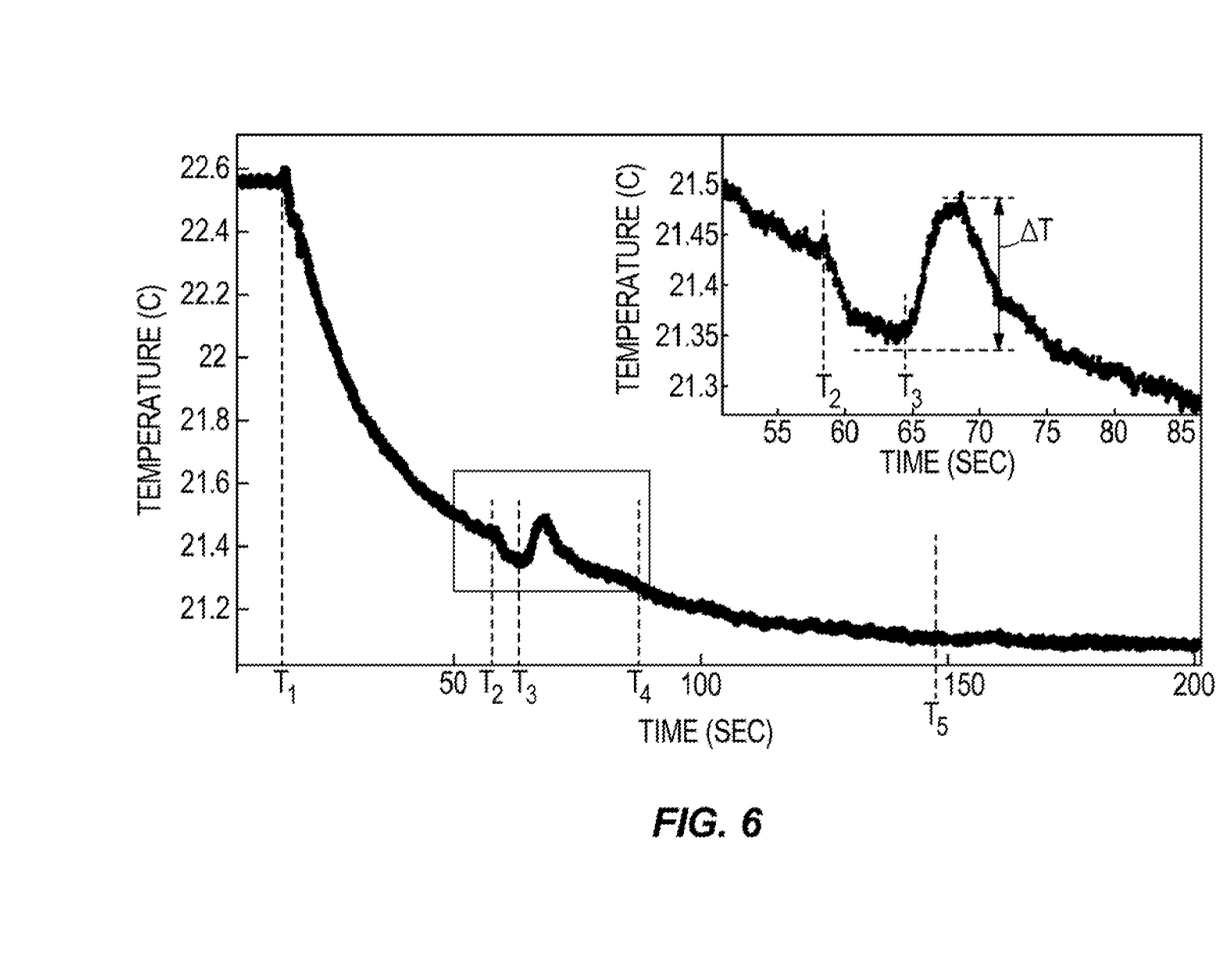
FIG. 6 is an exemplary graph of temperature measurements acquired by an embodiment of a sensor as disclosed herein.

At 110 the temperature detected by the RTD is measured over time. FIG. 6 is a graph of an exemplary temperature measurement by an RTD over time, exemplarily of a measurement of glucose concentration. It will be recognized that in embodiments, the temperature measurement 110 may begin prior to the introduction of the sample at 108 and continue through the reaction of the sample with the reagent. In the graph of FIG. 6, T1 represents the time at which the reagent is applied to the reaction site. Before T1 it will be noticed that the temperature of the RTD has stabilized at the self-heated temperature above ambient temperature. After the liquid sample is applied at T1, the temperature sensed by the RTD decreases. As the exemplary reagent is at or below ambient temperature and the RTD is above ambient temperature, after the reagent is applied at T1, the temperature sensed by the RTD drops.

Once the temperature of the sensor stabilizes again after introduction of the reagent (e.g. enzyme), the liquid sample is introduced at the sample inlet of the sample arm at time T2. In an exemplary embodiment, the microfluidic sensor may be constructed, assembled, or manufactured with the reagent already in place at the reaction site. In such an embodiment, the stabilization time between T1 and T2 would not be necessary. Rather, in operation a user may have to wait for the powered RTD to stabilize due to self-heating, which in FIG. 6 would have occurred prior to T1. The inset of FIG. 6 depicts of a close up view of a portion of the graph of FIG. 6 centered on the chemical reaction of the glucose with GOD enzyme reagent. The chemical reaction between the glucose in the liquid sample and the GOD enzyme reagent beings at time T3 when the liquid sample reaches the reagent. The temperature drops between times T2 and T3 is due to the temperature gradient between the RTD and the liquid sample and also be evaporation of the liquid sample. Starting at time T3, the chemical reaction occurs. Due to do the exothermic nature of the glucose oxidation process, the temperature rises and reaches a peak temperature. After which the temperature measured by the RTD drops as chemical reaction ends at T4 and the RTD reaches a new equilibrium with the surroundings at T5.

Referring back to FIG. 5 in conjunction with FIG. 6, at 112, as change in the detected temperature is calculated, exemplarily represented as $\Delta T$ in the graph of FIG. 6. This may exemplarily occur as the temperature is measured by the RTD. Next, at 114 the concentration of the target chemical is determined from the calculated change in the detected temperature. It will be recognized that in additional embodiments, the concentration is detected as a detection of a presence of the target chemical. In one such embodiment, the presence of the chemical may be indicated by a temperature spike due to a reaction with the reagent at a minimum calculated concentration threshold. In an exemplary embodiment, the following equation is used to correlate the peak of temperature change, $\Delta T$, to the concentration of glucose.

$$n_p = C_p \frac{\Delta T}{\Delta H} \tag{9}$$

where $\Delta H$ is molar enthalpy change, np is moles of product, and $C_p$ is the heat capacity of the system. The heat capacity (or thermal mass) of the system may be calculated by calibrating with a low concentration of the glucose test sample. Having an exact concentration of glucose, enthalpy change, and temperature change, the thermal mass of our system can be determined. The evaporation is also taken into account as a result of the device being calibrated.

In non-limiting embodiments the determination of the concentration from the change in effected temperatures at 114 may further include compensation of the determination for additional considerations including the reaction rate between the liquid sample and the reagent and the ratio of the reaction area to the total area of the RTD. The finite reaction rate is limited by the number of available reagent sites for the target substances. Therefore, some embodiments may account for reaction time in the determination of concentration. In doing so, a number of moles is calculated by the determined concentration and the volume size of the samples. This is compared to the regular number of molecules of the reagent to evaluate whether the reaction is in the saturated or unsaturated region of the reaction rate. The reaction rate can be modeled as linear for high concentrations near the saturation rate.

At 116 the determined concentration or presence is presented, exemplarily on a graphical display or other visual presentation of the determined concentration, including electronic messaging, illumination of an LED or other indicator, or a paper printout, or other forms of presentation as will be recognized by a person of ordinary skill in the art. In other embodiments, the determined concentration may be stored at a computer readable medium for later retrieval and review.

In another exemplary embodiment, a reagent of hydrogen peroxide reacts with intercellular iron from pharatin and catalyzes the formation of hydroxyl groups which cleave deoxyribonucleic acid (DNA). Therefore, hydrogen peroxide may be used as an exemplary reagent for a measure of photic chemical sensors configured to detect the presence or concentration of DNA. Such an embodiment may achieve a device for as low cost DNA concentration detection. Such a device has application as the purification of DNA after extraction is necessary for many sequencing approaches. This embodiment provides to low cost and simple way to monitor the concentration of DNA in the purified sample. In still further embodiments the generated heat as found in the graph of temperature over time during the course of the reaction may contain useful information about the DNA itself and its characterizations.

In a still further embodiment, a reagent of biotin may be used in an embodiment of a microfluidic chemical sensor to exemplarily detect the target chemical of streptavidin. Protein binding is used to identify or isolate different kinds of cells with related biomarkers as well as in diseased detection by studying the reaction of antibodies and antigens. In embodiments, rather than determining a concentration, microfluidic chemical sensors of this embodiment are directed to identify the existence of the target protein binding. In such an embodiment detection of protein binding maybe identified by a temperature spike in the temperature-time recording as compared to the normally expected temperature drops as shown in FIG. 6. Identification of such a temperature spike in the temperature-time recording provides a thermal detection of protein binding events in a label-free detection mechanism. Such embodiments may be used for portable disease detection kits. Often, protein binding detection relied upon another type of marking or labeling substance (e.g. chemiluminescence) that is detected in order to detect the protein binding. This introduces additional impurities into the samples and reagents and therefore embodiments of the disclosed microfluidic sensor that achieve label-free detection may be desired.

Figure 4:
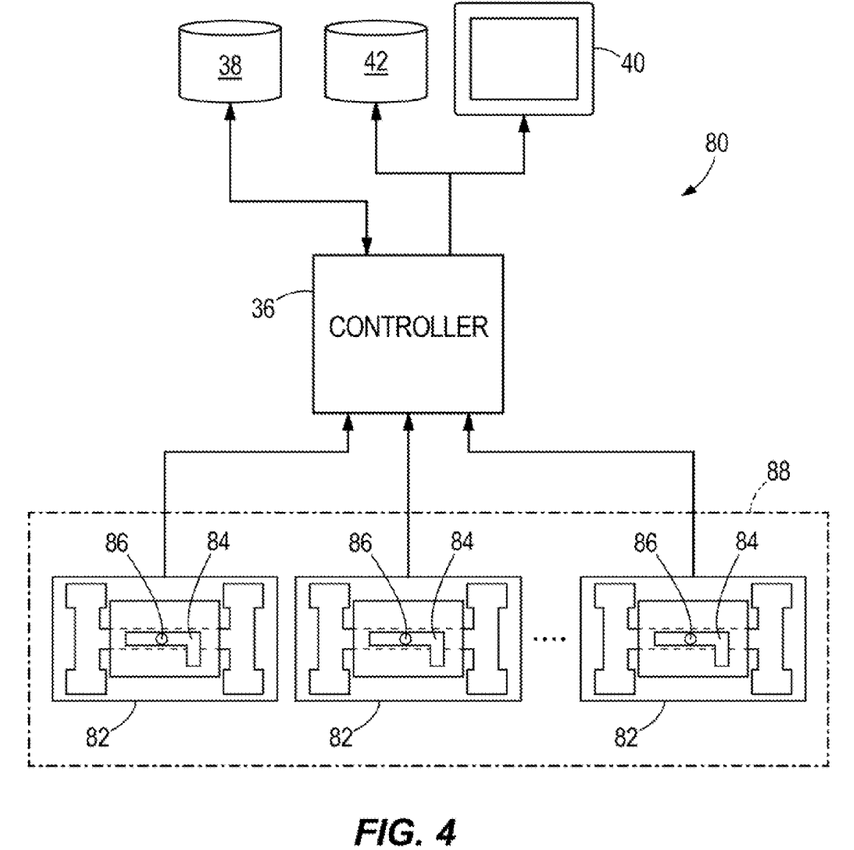
FIG. 4 is a schematic diagram of an additional exemplary embodiment of a system for sensing a chemical.

The calorimetric detection mechanism as a label-free method allows the expansion of applications of enzyme based sensors by a wide range of enzymatic reactions. FIG. 4 is a schematic diagram of an additional exemplary embodiment of a system 84 detecting the presence or concentration of a chemical. It will be recognized that like reference numerals between the system 80 of FIG. 4 and system 34 of FIG. 2 are used to denote like features between the disclosed embodiments and is used for brevity and conciseness in the present disclosure. It will be recognized by a person of ordinary skill in the art that various modification and/or features of the embodiments as disclosed herein may be used within the disclosed systems while remaining within the scope of the present disclosure.

In the system 80, multiple microfluidic chemical sensors 82 are each communicatively connected to the controller 36. It is to be recognized that the system 80 of FIG. 4 is highly schematic in nature and that the actual communicative connections between the microfluidic chemical sensors 82 and the controller 36 may be implemented in a suitable manner in accordance with the construction of the system and/or devices. In an embodiment, the system 80 includes a plurality of microfluidic chemical sensors arranged in a microarray 88 and configured to simultaneously provide multiple calorimetric tests to a liquid substance. In an exemplary embodiment, a different reagent 86 is placed in the microfluidic channel 84 of the respective microfluidic chemical sensors 82. In an exemplary embodiment, the reagents 86 may be a series of protein bonding samples and the microarray 88 is configured to test a liquid sample for the presence of a plurality of protein biomarkers. Such a microarray that simultaneously tests for the presence of a plurality of biomarkers may be used as a diagnostic or disease detection tool or kit. In use, the liquid sample is introduced to all of the microfluidic channels 84 and the controller 36 records the measured temperature over time from each of the microfluidic chemical sensors. As noted above, a spike in the temperature recording from one or more of the specific microfluidic chemical sensors 82 is indicative of the presence of the biomarker for which that microfluidic chemical sensor is configured to detect.

In embodiments, the device and system as disclosed herein may be used to sense the concentration of a wide variety of chemical or biological substances. While previous sensors as referenced above are limited to only those substances that produce a conductive or a color change effect upon reaction can be sensed, an advantage of embodiments of the device and system as described herein is the applicability to a wide range of substances to be sensed. As all chemical reactions/ interactions produce a change in entropy, this change can be translated into a measurement performed by an embodiment of the disclosed sensor.

Embodiments of the device and system as disclosed herein can be created for a wide variety of concentration sensing applications. Non-limiting examples of the types of applications in which embodiments of the presently disclosed device and system may be used can include, but are not limited to glucose concentrations found in a bodily fluid or alcohol concentrations found in a bodily fluid. In another application, an embodiment may be used to sense the concentration of oxygen in water. In a still further embodiment, the system or device may be used to analyze a concentration of a particular substance in the sweat of an athlete, such that the athlete can be informed of information such as, but not limited to body composition, work out effectiveness, or physiological condition. Still further embodiments of the device or system can be used in biological screening such as to detect the presence or concentration of a marker protein. Such embodiments may use, but are not limited to the use of an enzyme as the reagent in the sensor which is to react to or bind with the marker protein to be sensed.

The above disclosed embodiments and applications are intended to be merely exemplary, but it will be recognized that other embodiments or applications may exist within the scope of the present disclosure.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A microfluidic sensor, the microfluidic sensor comprising:
    a microchannel constructed of paper that comprises a reaction site that comprises a reagent and a sample inlet, wherein the microchannel is configured to receive a liquid substance comprising a chemical at the sample inlet that travels by capillary action to the reaction site;
    a temperature sensor located proximal the reaction site of the microchannel and configured to measure a temperature as a result of a reaction between the reagent and the chemical in the liquid substance; and
    a controller communicatively connected to the temperature sensor, the controller receives the temperature measured by the temperature sensor and derives a concentration of the chemical in the liquid substance from the temperature.

2. The microfluidic sensor of claim 1, further comprising a support layer to which the microchannel and the temperature sensor are secured.

3. The microfluidic sensor of claim 2, further comprising an adhesive layer disposed between the temperature sensor and the microchannel, wherein the adhesive layer electrically insulates the temperature sensor from the microchannel and secures the microchannel and temperature sensor to the support layer.

4. The microfluidic sensor of claim 1, wherein the temperature sensor is a resistive temperature detector.

5. The microfluidic sensor of claim 1, wherein the microchannel overlaps the temperature sensor in a region about the reaction site and the microchannel in the region about the reaction site is dimensioned in a width dimension to be less than a dimension of the temperature sensor in a width dimension.

6. The microfluidic sensor of claim 5, wherein the controller further operates to compensate the derived concentration of the chemical based upon the reaction rate between the reagent and the liquid substance.

7. The microfluidic sensor of claim 1, further comprising an enclosure defined about at least the temperature sensor and the reaction site.

8. The microfluidic sensor of claim 1, wherein the temperature sensor measures the temperature over time and the controller derives the concentration of the chemical in the liquid substance from a local maximum temperature change from a steady state temperature of the temperature sensor.

9. The microfluidic sensor of claim 1, wherein the sample inlet is a first sample inlet and the microchannel further comprises a second sample inlet and the first sample inlet and the second sample inlet are orthogonal to a portion of the microchannel that comprises the reaction site.

10. The microfluidic sensor of claim 1, wherein the reagent is selected to detect a predetermined target chemical in the liquid substance.

11. A microfluidic sensor system comprising:
    at least one microfluidic sensor, comprising:
        a microchannel constructed of paper that comprises a reaction site that comprises a reagent and a sample inlet, wherein the microchannel is configured to receive a liquid substance comprising a chemical at the sample inlet that travels by capillary action to the reaction site; and
        a temperature sensor located proximal the reaction site of the microchannel and configured to measure a temperature as a result of a reaction between the reagent and the chemical in the liquid substance;
    a controller communicatively connected to the at least one microfluidic sensor, the controller receives the temperature measured by the temperature sensor of at least one microfluidic sensor and derives a concentration of the chemical in the liquid substance from the temperature; and
    a graphical display operated by the controller to present the derived concentration of the chemical in the liquid substance.

12. The system of claim 11, wherein the at least one microfluidic sensor is a plurality of microfluidic sensors, each of the microfluidic sensors of the plurality comprising a different reagent configured to react with a different chemical and wherein the same liquid substance comprising a chemical is received at the sample inlets of each of the plurality of microfluidic sensors, and the controller operates to identify the chemical based upon the derived concentrations from the temperatures received from the plurality of microfluidic sensors.

13. The system of claim 12, wherein the controller is a central controller communicatively connected to each of the plurality of microfluidic sensors.

14. The system of claim 12, wherein the controller is one controller of a plurality of controllers, each of the controllers in the plurality being communicatively connected to one of the microfluidic sensors of the plurality of microfluidic sensors.

15. The system of claim 11, wherein the at least one microfluidic sensor further comprises:
    a support layer to which the microchannel and the temperature sensor are secured; and
    an adhesive layer disposed between the temperature sensor and the microchannel, wherein the adhesive layer electrically insulates the temperature sensor from the microchannel and secures the microchannel and temperature sensor to the support layer.

16. The system of claim 15, wherein the temperature sensor is a resistive temperature detector.

17. A microfluidic sensor, the microfluidic sensor comprising:
    a microchannel that comprises a reaction site on a first finger, the reaction site comprises a reagent, a sample inlet, and a second finger wherein the microchannel is configured to receive a liquid substance comprising a chemical at the sample inlet that travels by capillary action to the reaction site;
    a first temperature sensor located proximal to the reaction site on the first finger of the microchannel and configured to measure a first temperature as a result of a reaction between the reagent and the chemical in the liquid substance;

a second temperature sensor located proximal to the second finger of the microchannel and configured to measure a second temperature; and a controller communicatively connected to the first temperature sensor and the second temperature sensor, the controller receives the first temperature and the second temperature and the controller derives a concentration of the chemical in the liquid substance from a differential between the first temperature and the second temperature.

18. The microfluidic sensor of claim 17 wherein the microchannel is constructed of paper.

19. The microfluidic sensor of claim 17 wherein the temperature sensor is a resistive temperature sensor.

20. The microfluidic sensor of claim 17, further comprising:

a support layer to which the microchannel and the temperature sensor are secured; and an adhesive layer disposed between the temperature sensor and the microchannel, wherein the adhesive layer electrically insulates the temperature sensor from the microchannel and secures the microchannel and temperature sensor to the support layer.

\* \* \* \* \*